United States Patent
Fox et al.

(10) Patent No.: US 10,745,658 B2
(45) Date of Patent: Aug. 18, 2020

(54) CLARIFIED FERMENTED BEVERAGES, AND A METHOD THEREOF

(71) Applicants: David G. Fox, Chicago, IL (US); Anthony C. Vieira, Beaufort, SC (US); Jacob M. Mattson, Bellevue, NE (US)

(72) Inventors: David G. Fox, Chicago, IL (US); Anthony C. Vieira, Beaufort, SC (US); Jacob M. Mattson, Bellevue, NE (US)

(73) Assignee: Mark Anthony International SRL, St. Michael (BB)

( * ) Notice: Subject to any disclaimer, the term of this patent is extended or adjusted under 35 U.S.C. 154(b) by 0 days.

(21) Appl. No.: 16/101,797

(22) Filed: Aug. 13, 2018

(65) Prior Publication Data

US 2019/0345424 A1   Nov. 14, 2019

Related U.S. Application Data

(60) Provisional application No. 62/544,261, filed on Aug. 11, 2017.

(51) Int. Cl.
| | |
|---|---|
| *C12H 1/00* | (2006.01) |
| *C12H 1/07* | (2006.01) |
| *C12C 12/00* | (2006.01) |
| *C12C 5/00* | (2006.01) |
| *C12H 1/10* | (2006.01) |

(Continued)

(52) U.S. Cl.
CPC ............. *C12H 1/063* (2013.01); *C02F 1/66* (2013.01); *C07C 29/76* (2013.01); *C12C 5/004* (2013.01); *C12C 12/00* (2013.01); *C12H 1/00* (2013.01); *C12H 1/003* (2013.01); *C12H 1/10* (2013.01); *G01N 33/14* (2013.01); *C07C 29/74* (2013.01); *C12C 2200/31* (2013.01); *C12G 3/08* (2013.01)

(58) Field of Classification Search
CPC .......... C07C 29/76; C07C 29/74; C12H 1/063; C12H 1/00; C12H 1/10; C12H 1/003; C12C 11/003; C12C 5/004; C12C 12/00; C12G 3/08; C02F 1/66; G01N 33/14
See application file for complete search history.

(56) References Cited

U.S. PATENT DOCUMENTS

| | | | |
|---|---|---|---|
| 2,206,066 | A | 7/1940 | Wallerstein |
| 2,416,007 | A | 2/1947 | Joachim |

(Continued)

FOREIGN PATENT DOCUMENTS

| | | |
|---|---|---|
| CN | 1 616 635 A | 5/2005 |
| CN | 1616635 A | 5/2005 |

(Continued)

OTHER PUBLICATIONS

J.B. South, Variation in pH and Lactate Levels in Malts, May-Jun. 1996, pp. 155-159, vol. 102, J. Inst. Brew., Burton-on-Trent, United Kingdom (5 pages).

(Continued)

*Primary Examiner* — Jennifer Wecker

(57) ABSTRACT

A system and method in a process for making a fermented beverage (FB), such as a bright beer, and producing a clarified FB, using a caustic dosing system to neutralize naturally-present organic acids typically present in a the fermented beverage (such as a bright beer) to the salt forms of the organic acids, and removing or separated the salts to form the clarified fermented beverage or clarified bright beer.

27 Claims, 4 Drawing Sheets

(51) Int. Cl.
*G01N 33/14* (2006.01)
*C02F 1/66* (2006.01)
*C07C 29/76* (2006.01)
*C12G 3/08* (2006.01)
*C07C 29/74* (2006.01)

(56) References Cited

U.S. PATENT DOCUMENTS

| | | | |
|---|---|---|---|
| 2,892,718 A | 6/1959 | Stone | |
| 3,594,178 A | 7/1971 | Meisler | |
| 4,217,217 A | 8/1980 | Kay et al. | |
| 4,440,795 A | 4/1984 | Goldstein et al. | |
| 5,108,929 A * | 4/1992 | Segura | B01F 3/0865 |
| | | | 210/96.1 |
| 5,294,450 A | 3/1994 | Word et al. | |
| 5,480,665 A | 1/1996 | Smith | |
| 5,618,572 A | 4/1997 | Tripp et al. | |
| 6,495,180 B1 | 12/2002 | Gurol | |
| 6,748,849 B2 | 6/2004 | Wilson et al. | |
| 7,008,652 B2 | 3/2006 | Effler | |
| 8,128,787 B2 | 3/2012 | Wynn et al. | |
| 8,697,169 B2 | 4/2014 | Duan et al. | |
| 2003/0196955 A1* | 10/2003 | Hughes | B01D 61/04 |
| | | | 210/650 |
| 2004/0067280 A1 | 4/2004 | Bonnet et al. | |
| 2006/0088632 A1* | 4/2006 | Armes | C12H 1/04 |
| | | | 426/271 |
| 2007/0138093 A1* | 6/2007 | Bossler | B01D 61/022 |
| | | | 210/639 |
| 2007/0221552 A1* | 9/2007 | Denney | B01D 21/0093 |
| | | | 210/85 |
| 2008/0175963 A1* | 7/2008 | Pope | A47J 31/44 |
| | | | 426/231 |
| 2008/0317930 A1 | 12/2008 | Duffy et al. | |
| 2009/0053785 A1* | 2/2009 | Kelley | C12N 1/38 |
| | | | 435/165 |
| 2009/0169691 A1* | 7/2009 | Duan | C12H 1/14 |
| | | | 426/330.4 |
| 2009/0199866 A1* | 8/2009 | Kirkpatrick | A23L 2/50 |
| | | | 134/3 |
| 2011/0028767 A1* | 2/2011 | Kikuchi | C07C 29/76 |
| | | | 568/916 |
| 2011/0244092 A1* | 10/2011 | Kelleher | A23J 1/02 |
| | | | 426/281 |
| 2013/0330792 A1* | 12/2013 | Takeuchi | C12P 7/56 |
| | | | 435/139 |
| 2014/0127354 A1 | 5/2014 | Pratt et al. | |
| 2014/0127366 A1* | 5/2014 | Vason | A23L 2/02 |
| | | | 426/239 |
| 2014/0142352 A1* | 5/2014 | Dauner | C12P 7/16 |
| | | | 568/913 |
| 2014/0335226 A1* | 11/2014 | Bell | A23C 21/023 |
| | | | 426/61 |
| 2016/0288022 A1* | 10/2016 | Wright | B01D 21/2444 |

FOREIGN PATENT DOCUMENTS

| | | |
|---|---|---|
| CN | 101276225 A | 10/2008 |
| CN | 101705165 A | 5/2010 |
| CN | 101 276 225 B | 1/2011 |
| EP | 0 593 566 B1 | 2/1997 |
| EP | 3101114 | 12/2016 |
| JP | 2006109830 A | 4/2006 |
| KR | 10-2010-0084156 A | 7/2010 |
| PT | 105 008 A | 3/2013 |

OTHER PUBLICATIONS

G.C. Whiting, Organic and Metabolism of Yeasts During Fermentation of Alcoholic Beverages—A Review, Mar.-Apr. 1976, pp. 84-92, vol. 82, J. Inst. Brew., Bristol, United Kingdom (9 pages).

International Search Report and Written Opinion by the European Patent Office, dated Nov. 6, 2019, from related International Application No. PCT/US2019/046308 filed Aug. 13, 2019 (15 pages).

Supplemental International Search Report and Written Opinion by the Korean Patent Office (KIPO), publicly available Feb. 20, 2020, for related International Application No. PCT/US2019/046308, filed Aug. 13, 2019 (17 pages).

Supplemental International Search Report and Written Opinion by the Chinese Patent Office (CNIPA), publicly available Feb. 20, 2020, for related International Application No. PCT/US2019/046308, filed Aug. 13, 2019 (9 pages).

Supplemental International Search Report and Written Opinion by the Japanese Patent Office (JPO), publicly available Feb. 20, 2020, for related International Application No. PCT/US2019/046308, filed Aug. 13, 2019 (9 pages).

Supplemental International Search Report and Written Opinion by the USPTO, publicly available Feb. 20, 2020, for related International Application No. PCT/US2019/046308, filed Aug. 13, 2019 (8 pages).

Barnes, "The Complete Beer Fault Guide, v. 1.4", 2011, © Thomas Barnes, obtained from http://www.carolinabrewmasters.com/PDF/Complete_Beer_Fault_Guide.pdf (42 pages).

Dostalek, et al, "Immunochemical determination of gluten in malts and beers", Nov. 2006, Food Additives and Contaminants vol. 23 No. 11, pp. 1074-0178 (5 pages).

Written Opinion by the European Patent Office as International Preliminary Examining Authority, dated Jul. 13, 2020, from related International Application No. PCT/US2019/046308 filed Aug. 13, 2019 (9 pages).

* cited by examiner

CLARIFIED FERMENTED BEVERAGES, AND A METHOD THEREOF

CROSS-REFERENCE TO RELATED APPLICATION

This application claims the benefit of U.S. Provisional Application No. 62/544,261, filed on Aug. 11, 2017, the disclosure of which is incorporated by reference in its entirety.

BACKGROUND OF THE INVENTION

Field of the Invention

The present invention relates to the production of a fermented beverage.

Description of the Related Art

Traditional beer and malt beverage-making processes undergo several treatment steps to convert barley into a fermentable sugar extract that can be utilized to create a neutral malt base (NMB), a colorless, flavorless, and odorless solution that can be further processed to formulate malt beverages of varying flavors. Such processes are described in detail in U.S. Pat. Nos. 4,440,795, 5,294,450, 5,618,572, and 7,008,652, as well as U.S. Patent Publication 2014/0127354, the disclosures of which are incorporated by reference in their entireties. A neutral malt base (NMB) is but one example of a fermented beverage (FB).

Beverages based on barley have been historically produced in a malt house, converting barley to malted barley, and a brewhouse, converting malt into a malt extract also known as a wort. Malting involves steeping of barley kernels to promote germination, followed by kiln drying at elevated temperatures. A brewhouse-centered process, well known to persons skilled in the art, treats the malt to break down the starches within the malt into smaller sugars consisting mostly of mono-, di-, and trisaccharides to form a wort. The wort can then be further boiled and blended in specific percentages with other sugars and added hops to produce the final fermentation substrate that can be combined with yeast to produce ethyl alcohol. After fermentation is completed, the fermented product can then be filtered, treated, and decolorized to produce a clear and colorless NMB.

Production of a neutral tasting alcoholic beverage utilizing a hopped wort has been described in Canadian Patent No. 1,034,064, incorporated by reference in its entirety. The process as a starting material a low kiln malt with a soluble protein content of between 30% and 37% by weight, a moisture content of 5% to 6% and a diastase value of 150 to 240. This low kiln malt is then mixed with water at between 66° C. and 77° C., to form a mash and maintained in that temperature range to produce a wort. The thereby produced wort is then boiled for 10-40 minutes, mixed with a carbohydrate adjunct and a supplementary nitrogen source and fermented with brewer's yeast. U.S. Pat. No. 4,495,204, incorporated by reference in its entirety, also discloses production of a neutral tasting alcoholic beverage prepared by mashing a well modified standard brewers malt, which is mixed in an amount of from 2% to 20% with a fermentable carbohydrate and water at a temperature of between 80° C. and 90° C. in an amount of from 80% to 98%, to obtain a fermentable solution, which is then cooled, pitched with brewer's yeast, and fermented.

A particular organic acid, such as acetic acid, citric acid, or tartaric acid, naturally present in a flavored malt beverage can provide a level of tartness, sweetness, and/or astringency that can affect the flavor. On the other hand, excess levels of tartness, sweetness, and/or astringency resulting from a particular acid found within the NMB can create a flavor profile that is unacceptable to the consuming public. Conventional techniques used for processing an NMB, do not effect the removal of such organic acid forms.

The acidity of a NMB can be traced back to the mashing process of the malt that converts the starches into fermentable sugars. Typically, milled grain is mixed with hot water in a mash tun to create a cereal mash. At the high temperatures at which this process occurs, insoluble calcium salts can form, contributing to the decrease of the pH in the mash. (See South, J. B. "Variation in pH and Lactate Levels in Malts" (1996) *J. Inst. Brew.* 102:155-159, the disclosure of which is incorporated by reference in its entirety.) The resulting worts contain a pH ranging from about 5.4 to about 5.8, depending on the malt type and calcium content. Similarly, organic acids, particularly lactic acid, which are also found in the malts can have an additional pH lowering effect on the wort that is produced. Moreso, organic acids form in the batch or continuous fermentation process. (See Whiting, G C "Organic Acid Metabolism of Yeasts During Fermentation of Alcoholic Beverages—A Review" (1976) *J. Inst. Brew.* 82:84-92, the disclosure of which is incorporated by reference in its entirety).

Consequently, there remains a need for a clarifying process that produces an FB that reduces or eliminates the levels of organic acid forms.

SUMMARY OF THE INVENTION

The present invention provides methods and a system for making clarified fermented beverage (FB) having reduced or negligible levels of organic acids form.

In one embodiment, the clarified FB can be used to produce flavored malt beverages (FMB) with flavor profiles that may clash with acidic contaminants that are commonly and naturally present in FBs produced by their conventional methods. In some embodiments, the clarified FB is also colorless, flavorless, and odorless.

In an embodiment of the invention, a method is provided for producing a clarified FB comprising the steps of: a) treating the fermented beverage (FB) by adding an alkaline treating agent to the FB to neutralize an acidic contaminants present in the FB, and b) removing the neutralized acidic contaminants from the treated FB to produce a clarified FB.

In another embodiment of the invention, a method is provided for producing a clarified FB, comprising the steps of: (a) providing a fermented beverage comprising at least one acidic contaminant; (b) neutralizing the at least one organic acidic contaminant by titrating or adding into the fermented beverage a sufficient amount of an alkaline treating agent to convert substantially all of the at least one acidic contaminant into an organic salt to form a neutralized fermented beverage; and (c) filtering out the organic salt, thereby producing a clarified fermented beverage (FB).

In an alternative embodiment of the invention, a method is provided for producing a clarified neutral malt base (NMB), comprising the steps of: (a) providing a bright beer comprising at least one acidic contaminant; (b) neutralizing the at least one organic acidic contaminant by titrating or adding into the bright beer a sufficient amount of an alkaline treating agent to convert substantially all of the at least one acidic contaminant into an organic salt to form a neutralized bright beer; and (c) filtering out the organic salt, thereby producing a clarified neutral malt base (NMB).

The alkaline treating agent can be a basic compound that is capable of reacting with an organic acidic contaminant, including both strong and weak bases. In some embodiments, the alkaline treating agent is a caustic comprising at least one Arrhenius base that increases the concentration of hydroxide ions in a solution with water. Non-limiting examples include Group I and Group II metal hydroxides such as potassium hydroxide, sodium hydroxide, barium hydroxide, cesium hydroxide, strontium, hydroxide, calcium hydroxide, lithium hydroxide, and rubidium hydroxide. In a further embodiment, the caustic comprises up to about 50% by weight sodium hydroxide.

In other embodiments, the alkaline treating agent is a caustic that is a weak base, in which the base and its conjugate acid are present in an equilibrium with each other. In a further embodiment, the alkaline treating agent comprises up to 50% by weight sodium bicarbonate.

In an embodiment of the invention, a method is provided for neutralizing at least one organic acidic contaminant in a fermented beverage solution, which can include a bright beer solution, comprising the steps of: (1) providing a quantity of a stream of fermented beverage containing an organic acidic contaminant; (2) introducing a neutralizing quantity of an alkaline treating agent into the fermented beverage stream, to adjust the pH of the fermented beverage stream into and within a target pH range sufficient to neutralize the organic acidic contaminants within the fermented beverage stream; (3) detecting the pH of the treated fermented beverage stream; and (4) adjusting the neutralizing quantity of the alkaline treating agent based on the detected pH of the treated fermented beverage stream, to maintain the pH of the treated fermented beverage within the target pH range.

In another embodiment, the quantity of the stream of fermented beverage has a mass or volumetric flow rate, and the neutralizing quantity of an alkaline treating agent has a mass or volumetric flow rate. In one embodiment, the mass or volumetric flow rate of the fermented beverage stream is substantially constant. In another embodiment the mass or volumetric flow rate of the fermented beverage stream is detected, and the adjusting of the neutralizing quantity of the alkaline treating agent is based on the detected pH of the treated fermented beverage and the mass or volumetric flow rate of the bright fermented beverage.

In an embodiment of the invention, the step of treating the fermented beverage (FB) to neutralize an acidic contaminants present in the FB, comprises the steps of: i) providing a contained quantity of the fermented beverage comprising the acidic contaminants; titrating a sample of the contained quantity of fermented beverage with an alkaline treating agent sufficient to neutralize the acidic contaminants in the sample to a salt form; and adding a quantity of an alkaline treating agent to the contained quantity of fermented beverage to treat the fermented beverage by neutralizing the acidic contaminants in the contained quantity to a salt form, wherein the quantity of the added alkaline treating agent is determined based on the titration of the sample. The alkaline treating agent used to treat the contained quantity of fermented beverage can be the same alkaline treating agent used to titrate the sample, or can be a different alkaline treating agent in a stoichiometric-equivalent quantity.

In another embodiment of the invention, the step of neutralizing the at least one organic acidic contaminant is performed in batch (or continuous batch) system, comprising: (a) container for a quantity of fermented beverage comprising an acid contaminants; (b) a pH meter for detecting the pH of the contained quantity of fermented beverage; (c) a metering means for introducing a controlled amount of an alkaline treating agent into the contained quantity of fermented beverage; and (d) a controller, for example a central programmable logic controller, in communication with the pH meter and the metering means. The metering means can be a metering pump or a liquid flow controller.

In an embodiment of the invention, the step of neutralizing the at least one organic acidic contaminant is performed in an in-line, caustic dosing system, comprising: (a) a piping system for fermented beverage streams; (b) one or more pH meter for detecting the pH of the fermented beverage stream, or the treated fermented beverage stream, or both; (c) an alkalinity container for the alkaline treating agent; (d) a metering means for introducing a controlled amount of the alkaline treating agent into the fermented beverage stream; and (e) a controller, for example a central programmable logic controller, in communication with the one or more pH meter and the metering means. The metering means can be a metering pump or a liquid flow controller.

In further embodiments, the at least one acidic contaminant in the fermented beverage is neutralized within the in-line caustic dosing system according to the steps of: (1) introducing the fermented beverage stream comprising an organic acid into the in-line caustic dosing system; (2) detecting the pH of the fermented beverage stream using a pH meter; (3) determining a neutralizing quantity of the alkaline treating agent sufficient to neutralize the organic acidic contaminants within the fermented beverage stream, using the controller; and (4) dispensing the neutralizing quantity of the alkaline treating agent from the alkalinity container into the fermented beverage stream downstream of the detection by the pH meter using a metering means, to form the treated fermented beverage stream. In a further embodiment, the in-line caustic dosing system can comprise a pH meter for detecting the pH of the fermented beverage stream at a position downstream of where the alkaline treating agent is introduced and mixed into the fermented beverage stream or for detecting the pH of the treated fermented beverage stream, or both. The detected pH of the treated fermented beverage stream is used by the controller to determine the sufficient neutralizing quantity of alkaline treating agent.

In some embodiments, the method can further include a removal step that can be performed subsequent to neutralizing the organic acidic contaminants within the fermented beverage, to remove the salt forms of the organic acid contaminants after neutralization. In an embodiment, the removal step comprises a filtering step, and passing the treated fermented beverage through a filter to separate and remove the salt forms of the organic acid contaminants. Typically, a suitable filter can include a filter or separate device sufficient for the desalination of sea water. Non-limiting examples of methods and systems for desalination include vacuum distillation, multi-stage flash distillation, multiple-effect distillation, vapor-compression distillation, reverse osmosis, freeze-thaw systems, solar evaporation systems, and electrodialysis reversal. See https://en.wikipedia.org/wiki/desalination), the disclosure of which is incorporated by reference in its entirety. In other embodiments, the method can also include filtration of the fermented beverage prior to neutralizing the organic acidic contaminants within the fermented beverage, to remove other particulate or filterable component.

In other embodiments, the invention also provides a neutralization system for neutralizing a fermented beverage stream to produce a clarified FB, comprising: (a) an in-line caustic dosing system for neutralizing the organic acidic contaminant in the bright beer stream; and (b) a filter or other device for separating out the salt forms of the organic acidic contaminants from the treated fermented beverage stream. In a further embodiment, the in-line caustic dosing system comprises one or more pH meter configured for monitoring the pH of the fermented beverage stream, the treated fermented beverage stream, or both; a container for an alkaline treating agent; a metering means for the alkaline treating agent; and a central programmable logic controller that is configured to monitor the pH of the fermented beverage stream, the treated fermented beverage stream, or both, detected by the one or more pH meter, and to control the amount of the alkaline treating agent dispensed from the container by the metering means.

These and other embodiments of the present invention will be apparent to one of ordinary skill in the art from the following detailed description.

DETAILED DESCRIPTION OF THE INVENTION

Definitions

Figure 1:
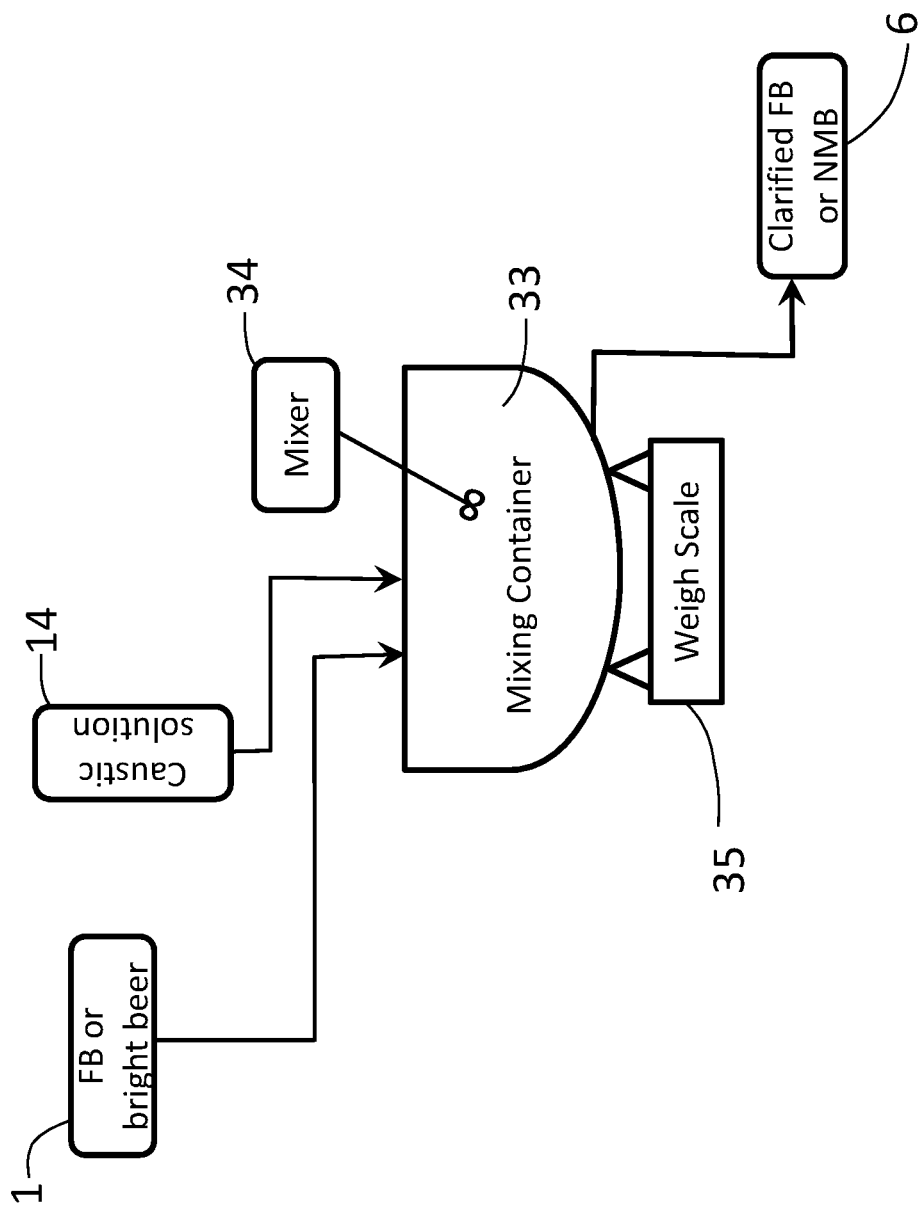
FIG. 1 shows a schematic diagram of a caustic dosing system and process for neutralizing organic acids in a fermented beverage solution, using a batch neutralizing system.

As used herein, the term, "and/or" when used in the context of a listing of entities, means the entities being present singly or in combination. Thus, for example, the phrase "A, B, C, and/or D" includes A, B, C, and D individually, but also includes any and all combinations and sub-combinations of A, B, C, and D.

As used herein, the terms, "bright beer" or "brite beer" means the crude, ethyl alcohol-containing liquid product of fermentation, after yeast has been decanted, filtered, or otherwise removed, and the term "treated bright beer" refers to the solution of bright beer after neutralizing or treatment with an alkaline treating agent.

As used herein, the term, "caustic" means a compound that dissociates completely to yield hydroxide ions upon interacting with water to form a solution that has a strongly basic pH. Such compounds include, but are not limited to Group I and Group II hydroxides such as potassium hydroxide, sodium hydroxide, barium hydroxide, cesium hydroxide, strontium, hydroxide, calcium hydroxide, lithium hydroxide, and rubidium hydroxide.

As used herein, the term, "fermented beverage" means a liquid beverage solution that is the product of fermentation, typically after any yeast has been or removed, containing ethyl alcohol or not.

As used herein, the term, "flavored malt beverage" means the final malt beverage product that is formed once the neutral malt base has been filtered, treated, and processed in order to produce a consumable beverage product. One non-limiting example of a flavored malt beverage is beer.

As used herein, the terms, "mash" or "mashing" means the process of converting the starches typically present in malts to lower-order sugar molecules, including monosaccharides, disaccharides, and trisaccharides, that are suitable for fermentation with yeast to produce an ethyl alcohol.

As used herein, the terms, "neutralize" or "neutralizing" means the neutralization of acids, including organic acids, in the neutral malt base with an alkaline treating agent to form therefrom organic salts.

As used herein, the terms, "neutral malt base" or "malt beverage base" means the ethyl alcohol-containing liquid formed as a result of filtering, treating and/or decolorizing the bright beer.

As used herein, the terms, "wort" or "malt extract" means the sugar-rich solution or mixture resulting from the mashing process that is suitable for fermentation with yeast to produce ethyl alcohol.

The present invention employs a fermented beverage that contains a measurable level of organic acids and/or other acid contaminants resulting from the processing to produce the fermented beverage. One type of fermented beverage is a neutral malt base (NMB). To illustrate the systems and processes of the present invention for fermented beverages generally, one or more systems or processes using a bright beer solution or stream to make a neutral malt beverage (NMB).

Making of a Neutral Malt Base

The present invention provides a clarified neutral malt base (NMB) that is colorless, flavorless, odorless, typically having a substantially neutral pH and containing a reduced or negligible level or amount organic acidic contaminant as compared to the level or amount in the bright beer, as well as a method and a system for producing the same. The method includes a step in which an alkaline treating agent is added to the bright beer stream to react with organic acids present in the bright beer stream to form organic salts, which can then be separated from the treated bright beer to produce a clarified NMB. In some embodiments, a flavored malt beverages (FMB) produced from the clarified NMB can have a more pleasing taste profile as a result of removing organic acids naturally present after the mashing process. In other embodiments, removing organic acids from the NMB creates a more versatile NMB to which any kind of flavoring agent can be added, particularly those that would otherwise create an unpleasant tasting FMB in combination with acids naturally present in a conventional NMB.

Traditional methods of brewing an FMB are widely known in the art and particularly described in detail in U.S. Pat. Nos. 4,440,795, 5,294,450, 5,618,572, and 7,008,652, as well as U.S. Patent Publication 2014/0127354, the disclosures of which are incorporated by reference in their entireties. Generally, to produce a conventional NMB, a supply of malt must first be obtained. The malt may be of any conventional type known in the art which is suitable for producing beer and other brewed beverages. One non-limiting example of a suitable malt is "Brewers Malt," available from Briess Malt & Ingredients Co. The malt is then combined with deionized water and heated at high temperature to produce a mash. At this stage, the mash will contain various malt-derived fermentable sugars (e.g. including but not limited to maltose and maltotriose), which are fermentable by yeast into ethyl alcohol, as well as several malt-derived non-fermentable sugars (e.g. including but not limited to maltotetraose and maltopentaose) that cannot be broken down into ethyl alcohol by yeast.

However, during the mashing process, precipitation of phosphate and proteins from the malts can result in the formation of insoluble calcium salts, which have been strongly correlated with a decrease in the pH of the mash product. In mash processes that utilize deionized water, the only possible source of calcium is from the malt itself. Additionally, several malt varieties contain high levels of lactate (See South, J. B. "Variation in pH and Lactate Levels in Malts" (1996) *J. Inst. Brew.* 102:155-159, the disclosure of which is incorporated by reference in its entirety), acetate, butyrate, propionate that ultimately are transferred to the mash. For instance, South determined that the concentration of lactate in several varieties of malts ranged from 17.6 to 126.3 milligrams per 100 grams of malt (dry weight). The lactate concentration is inversely proportional to the pH of the wort, ranging from 5.59 at the highest lactate concentration to 6.02 at the lowest lactate concentration.

After the mash product has been generated, several processes known in the art can be utilized to generate a sugar-rich wort that is suitable for fermentation. Such processes include, but are not limited to, adding enzymes that are capable of breaking down the starches and/or sequentially heating the mash to catalyze chemical conversion of the starches into sugars.

Next, the mash is physically treated in order to remove solids therefrom, using any apparatus known in the brewing art for filtering mash. The liquid filtrate, which is colloquially known as the wort or malt extract, can then be collected and transferred to a brew kettle in the presence of additional fermentable sugars (e.g. dextrose, sucrose, and/or corn syrup) and optionally, "hop materials," which can encompass a wide variety of different products, including but not limited to hop cones, pre-isomerized pelletized hops, and/or solvent-extracted concentrated hop extract. Yeast can then be added to the wort to initiate fermentation, which is allowed to continue until there are no fermentable sugars remain. Typically, the fermentation process can last for 7-11 days, but the fermentation time is ultimately dependent on numerous factors, including but not limited to temperature. Warmer temperatures typically result in faster fermentation, although excessive heat can create several issues and is often avoided.

After fermentation is completed, the yeast from the alcohol-containing fermented product is allowed to settle out of the product and removed by conventional decantation or filtering techniques, forming a bright beer. Bright beer is usually colored, fragrant, and unsuitable for use in make an FMB. In contrast, the NMB used for making an FMB is colorless, flavorless, and odorless. However, acids, including organic acids, in the mash product are retained throughout the entire brewmaking process, and none of the filtering or purification techniques address the organic acidic contaminant that can often contribute to undesired tastes or odors when mixed with certain flavor additives to form an FMB.

Embodiments of the Invention

In some embodiments, the present invention provides a method of producing a clarified fermented beverage (including NMB) from a fermented beverage solution comprising one or more organic acidic contaminant, comprising the steps of: (a) neutralizing a one or more organic acidic contaminant contained in the fermented beverage solution by titrating or adding into the fermented beverage an amount of an alkaline treating agent sufficient to convert substantially all of the at least one organic acidic contaminant into its conjugate base to form an organic salt; and (b) removing the organic salt, thereby producing a clarified fermented beverage (or clarified NMB). In an embodiment of the invention, the sufficient amount of alkaline treating agent is sufficient to change the pH of the bright beer to within a pH range of 5.5 to 8.5, including a pH of at least about 5.8, or at least about 5.9, or at least about 6.0, and up to about 7.5, or up to about 6.3, or up to about 6.1. In another embodiment, the pH target or range is about 6.0±0.1. Similarly, the clarified fermented beverage has a buffered pH within a pH range of 5.5 to 8.5, including a buffered pH of at least about 5.8, or at least about 5.9, or at least about 6.0, and up to about 7.5, or up to about 6.5, or up to about 6.3. As described above, the organic acidic contaminants can arise from the malt itself or from precipitation of phosphates or proteins within the malts during the mashing process. Organic acidic contaminants can include, but are not limited to, organic carboxylic acids such as acetic acid, lactic acid, propionic acid, and butyric acid.

After removal or separation of the salt forms of the organic acidic contaminants from the pH-treated bright beer solution, the buffered pH of the clarified NMB may have a slightly different and partly lower, or partly higher pH than the pH of the unfiltered pH-treated bright beer, depending on the pKa of the organic acids.

The alkaline treating agent can be any basic compound that is capable of reacting with an acidic contaminant, including both strong and weak bases. Suitable strong bases can include, but are not limited to, a caustic comprising at least one Arrhenius base that increases the concentration of hydroxide ions in a solution with water, such as the Group I and Group II metal hydroxides potassium hydroxide, sodium hydroxide, barium hydroxide, cesium hydroxide, strontium, hydroxide, calcium hydroxide, lithium hydroxide, and rubidium hydroxide. Stock solutions of the caustic can be any concentration, but the concentration should be sufficiently high to safely add a minimal amount of the caustic to neutralize the acidic contaminants within the bright beer without substantially affecting its volume. In some embodiments, the caustic comprises a 50% (v/v) solution of sodium hydroxide. Upon reacting with one of the metal hydroxides listed above, the at least one acidic contaminant is converted to a salt and water, according to net ionic equation in Equation 1, below.

$$HA(aq) + OH^-(aq) \rightarrow A^-(aq) + H_2O(l) \tag{1}$$

When the acidic contaminant is acetic acid, the neutralization reaction proceeds according to Equation 2, shown below.

$$CH_3COOH(aq) + OH^-(aq) \rightarrow CH_3COO^-(aq) + H_2O(l) \tag{2}$$

In other embodiments, the alkaline treating agent can be a weak base. Generally, a weak base does not dissociate completely in water and can exist in equilibrium with its conjugate acid. As with the strong bases, enough of a weak base must be added to completely neutralize the acids present in the bright beer. Suitable weak bases can include, but are not limited to sodium acetate, sodium bicarbonate, and ammonium hydroxide. In some embodiments, the alkaline treating agent is ammonium hydroxide. The equation of the neutralization reaction between acetic acid and ammonium hydroxide is shown below in Equation 3.

$$CH_3COOH(aq) + NH_4OH(aq) \leftarrow CH_3COONH_4(aq) + H_2O(l) \tag{3}$$

However, in any reaction between a weak acid and a weak base, the resulting net ionic equation results in the production of water, according to Equation 4, below.

$$H^+(aq) + OH^-(aq) \leftarrow H_2O(l) \qquad (4)$$

Effectively, the neutralization of the at least one acidic contaminant can be accomplished by titrating into the bright beer a sufficient amount of the alkaline treating agent to convert most or all of the organic acidic contaminants that are present, to a salt or filterable form thereof. Within an industrial brewmaking process, bright beer can be neutralized in single batches that must attain a specific pH before being pumped to the next station/processing step, or over the course of a continuous process as the bright beer is constantly pumped from one location to another. Several instrumentation and electrode systems for monitoring and adjusting the pH of a liquid are known in the art. Such non-limiting examples include batch processing, in-line processing, and continuous stirred-tank pH monitoring and dosing systems, for example, available from Omega Engineering, located in Stamford, Conn.

In an embodiment of the invention illustrates in FIG. 1, a caustic dosing system and method can include a mixing container for holding a determined quantity of a fermented beverage (FB) or bright beer containing organic acids. The determined quantity of the FB or bright beer can be based on mass, such as by a weigh scale 35 for the contents of the container 33, by a volume indicator in the container 33, or by the delivery of a volumetric amount of the FB or bright beer into the container 33. After the determined quantity of the FB or bright beer is treated to neutralize the organic acids, the treated FB or determined quantity of the FB or treated bright beer can be emptied from the container 33 to a post-filtration or separation apparatus 4 to remove the salt forms of the organic acids.

A simple though effective method for treating the FB or bright beer can comprise the following steps. A quantity of the fermented beverage that comprises the acidic contaminants in fed into the container, either as determined or pre-determined mass or volume of the FB. An assay is performed on a small known quantity of the FB by titrating into the stirred, known quantity of the FB a known alkali solution containing an alkali ingredient of known concentration. The sample of the contained quantity of fermented beverage is titrated with the alkali solution by well-known means sufficient to neutralize the solution to a pH at which the organic acids and other acidic contaminants in the sample form a salt. Using well known calculations, an amount of the same or different alkaline treating solution is determined that is sufficient to neutralize the organic acids in the contained quantity of the FB, and is added into the contained quantity of the FB under mixing. The alkaline treating agent used to treat the contained quantity of fermented beverage can be the same alkaline treating agent used to titrate the sample, or can be a different alkaline treating agent in a stoichiometric-equivalent quantity. The treated contained quantity of the FB is emptied from the container to a post-filtration or separation apparatus to remove the salt forms of the organic acids.

Figure 2:
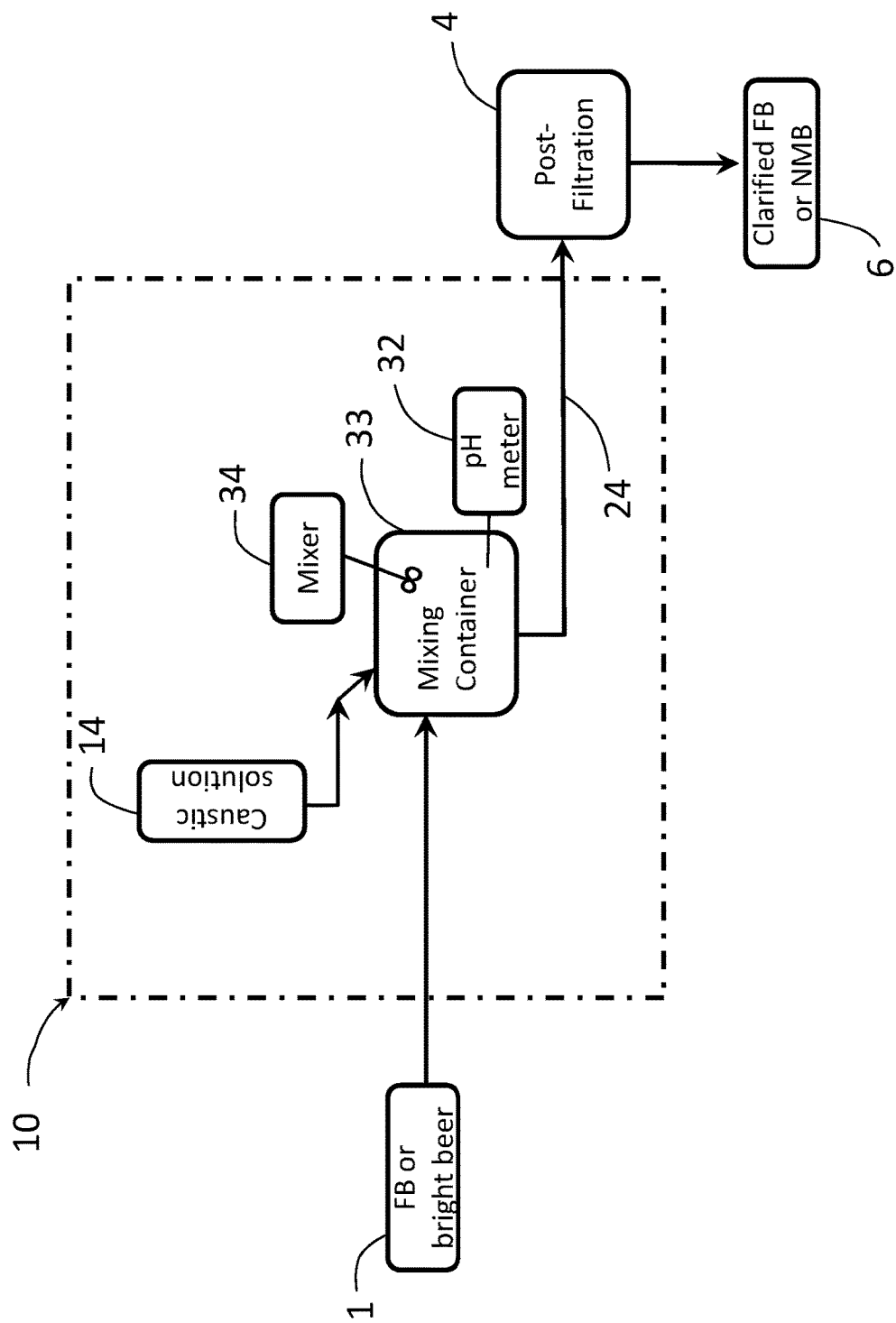
FIG. 2 shows a schematic diagram of a caustic dosing system and process for neutralizing organic acids in a fermented beverage solution, using a continuous-batch neutralizing system.

In an even further embodiment, the invention provides a method for producing a clarified NMB, comprising the steps of (a) providing a bright beer comprising at least one acidic contaminant; (b) neutralizing the bright beer by titrating a sufficient amount of an alkaline treating agent into the bright beer to convert substantially all of the at least one acidic contaminant from the bright beer into an organic salt to produce a treated bright beer; and (c) separating the salt forms of the organic acids from the neutral bright beer to produce an NMB product In another embodiment shown in FIG. 2, the caustic dosing system 210 can have a mixing means that includes a continuous-batch or batch mixing container 33 that retains a volume of treated bright beer solution, with a mixing device 34 for homogenizing the solution, and a pH meter for detecting the pH thereof, retained in the container 33. A pH meter 32 in communication with the controller 26 detects the pH of the treated bright beer solution retained in the tank, and the controller 26 adjusts the sufficient quantity of the caustic solution metered into the container 33 based on the rate or quantity of bright beer stream 20, and the pH of the treated bright beer solution as measured by the pH meter 32, or by the pH of the bright beer stream 20, or both. In this embodiment, the outflow of treated bright beer solution 24 can be substantially continuous.

In an embodiment wherein the container 33 is a batch mixing tank, a quantity of bright beer solution 1 is loaded into the tank 33, and a controlled quantity of caustic solution is passed or metered into the batch quantity of bright beer solution until a pH in the target pH range is achieved. The batch of pH-treated bright beer is then discharged from the tank 33 to post-filtration 4.

Figure 3:
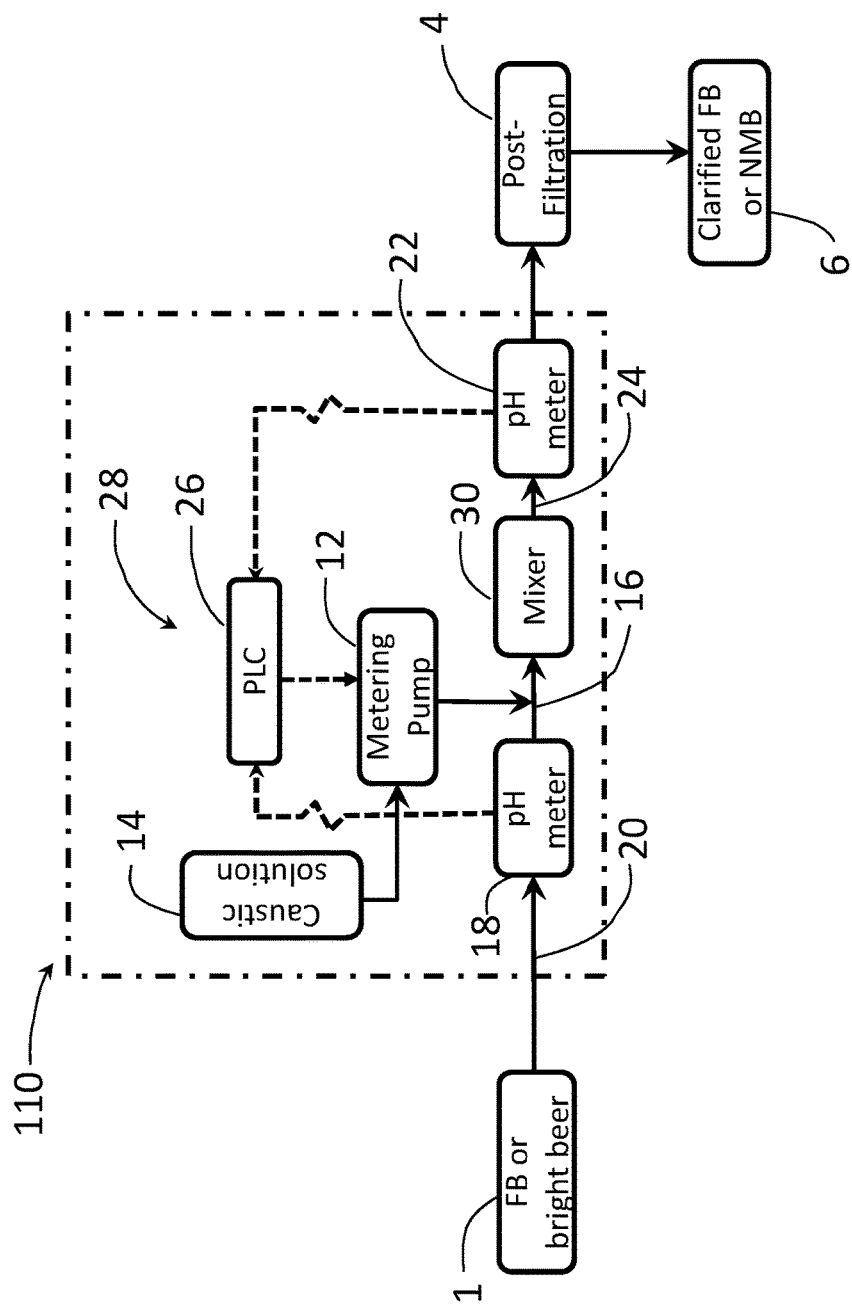
FIG. 3 shows a schematic diagram of a caustic dosing system and process for neutralizing organic acids in a fermented beverage solution, using an in-line continuous neutralizing system, employing a caustic solution metering pump.

In an embodiments illustrated in FIG. 3, the pH monitoring and dosing system is an in-line caustic dosing system. The caustic dosing system 110 processes a fermented beverage (FB), or bright beer, stream 1 into an outflow of a clarified NMB 6. The bright beer solution 1 passes to the caustic dosing system 10, and after pH treatment of the bright beer solution in the caustic dosing system 10, the resulting pH-treated bright beer 24 is processed by post-filtration 4 to remove or filter the salt forms of the organic acids, to produce the clarified fermented beverage (FB) or neutral malt beverage (NMB) 6.

The caustic dosing system 110 includes a metering means, illustrated as a metering pump 12, for metering a quantity of a caustic solution from a container 14 for the caustic solution into a junction of the piping system 16 disposed between two pH meters, including a first pH meter 18 that detects the pH of the bright beer solution entering 20 the caustic dosing system 10, and a second pH meter 22 that detects the pH of the treated bright beer solution 24 after the addition of the caustic solution. The two pH meters 18 and 22 and metering pump 12 are in data signal transfer and control communication with a programmable logic controller (PLC) 26 to form a communication and control loop 28 that detects pH of the bright beer solutions, determines an amount of caustic solution sufficient to neutralize organic acidic contaminants in the bright beer, and controls the quantity and/or rate of caustic solution added to the bright beer solution that is sufficient to neutralize the bright beer solution to a target pH range sufficient to neutralize the organic acidic contaminants within the beer stream. The concentrated caustic stock solution can be a 50% (wt/wt) solution of sodium hydroxide.

Typically, the pH of bright beer entering the caustic dosing system is less than about 6.0. However, the pH can vary according to the identity and concentration of the acidic contaminants within the bright beer. For instance, the pKa values of acetic acid, lactic acid, propionic acid, and butyric acid are 4.75, 3.86, 4.87, and 4.82, respectively. As reported by Smith, (see "Variation in pH and Lactate Levels in Malts," above) the concentration of lactate in various malt varieties ranged from 17.6 to 126.3 milligrams per 100 grams of malt. Based on the pH of the bright beer entering the caustic dosing system determined at the pH meter 18, the PLC 26 determines the amount of caustic solution to add into the bright beer stream by metering pump 12 to raise the pH to within the target pH range to neutralize the acidic contaminants.

The second pH meter 22, located on the outflow side of mixing means, discussed below, provides feedback control by communicating to the PLC 26 of the pH of the pH-treated bright beer stream after caustic solution is injected or added. In an embodiment of the invention, after the bright beer stream has passed through the caustic dosing system 10, the neutralized or treated bright beer has a pH sufficient to neutralize the organic acid contaminants. The PLC 26 can be configured to increase or decrease the amount or rate of caustic solution injected by the caustic dosing system 10 until the pH of the neutralized (treated) bright beer is within the target pH range.

The caustic dosing system 10 can also include a mixing means for mixing the stream of bright beer and the caustic solution into a homogenous pH-treated solution having a pH that has been adjusted into the target pH range. The mixing means ensure homogeneity of the pH-treated solution and improves the neutralization control and outcome. One embodiment of a mixing means is an in-line mixer 30, such as a static in-line mixer, as shown in FIG. 3.

Figure 4:
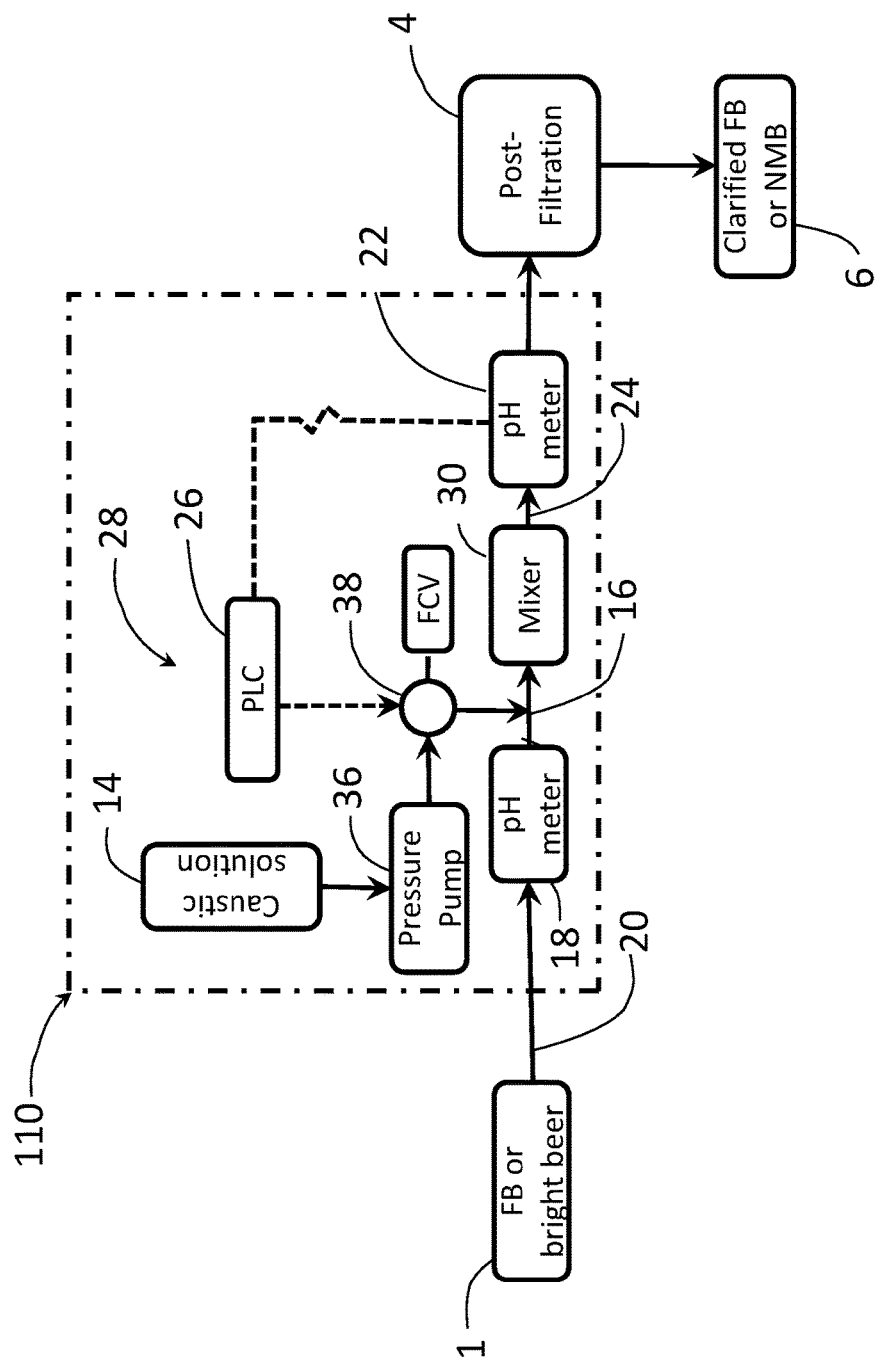
FIG. 4 shows caustic dosing system and process similar to FIG. 3, employing a caustic flow control valve pump.

In an alternative embodiment of a caustic dosing system 110 shown in FIG. 4, the sufficient quantity of caustic solution is controlled using a flow control valve (FCV) 38 that regulates the solution under pressure from a pressure pump 36. It will be clear and obvious to persons of ordinary skill in the art that there are other apparatus, devices and system that can be employed to control a sufficient quantity and/or rate of caustic solution.

In other embodiments, the alcohol content of a clarified NMB is at least about 5 percent, including at least about 10, at least about 12, at least about 15, at least about 17, and at least about 20 percent by volume of the NMB. In other embodiments, the alcohol content of a clarified NMB is less than or equal to about 20, including less than or equal to about 17, less than or equal to about 15, less than or equal to about 12, less than or equal to about 10, and less than or equal to about 5 percent, by volume of the NMB. Useful ranges can be selected from any value between and inclusive of about 5 percent to about 20 percent by volume of the NMB, including from about 5 percent to about 20 percent by volume, from about 10 percent to about 20 percent by volume, from about 12 percent to 20 percent by volume, from about 15 percent to about 20 percent by volume, from about 17 percent to about 20 percent by volume, from about 10 percent to about 17 percent by volume, or from about 12 percent to about 15 percent by volume. In a further embodiment, the clarified NMB further comprises hops.

In some embodiments, the invention provides a neutralization system for neutralizing a bright beer to produce a clarified NMB having substantially neutral pH organic acid forms, comprising: a beer stream, an in-line caustic dosing system, and at least one filtration or separation apparatus configured to filter out the salt forms of the acid contaminants from the beer stream. The in-line caustic dosing system can comprise at least one pH meter for monitoring the pH of the beer stream, a container for an alkaline treating agent, a metering pump, and a central programmable logic controller (PLC) that is configured to monitor the pH of the beer stream collected by the at least one pH meter and to control the amount of the alkaline treating agent dispensed from the container by the metering pump.

While particular embodiments of the invention have been described, the invention can be further modified within the spirit and scope of this disclosure. Those skilled in the art will recognize, or be able to ascertain using no more than routine experimentation, numerous equivalents to the specific procedures, embodiments, claims, and examples described herein. As such, such equivalents are considered to be within the scope of the invention, and this application is therefore intended to cover any variations, uses or adaptations of the invention using its general principles. Further, the invention is intended to cover such departures from the present disclosure as come within known or customary practice in the art to which this invention pertains and which fall within the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

The contents of all references, patents, and patent applications mentioned in this specification are hereby incorporated by reference, and shall not be construed as an admission that such reference is available as prior art to the present invention. All of the incorporated publications and patent applications in this specification are indicative of the level of ordinary skill in the art to which this invention pertains, and are incorporated to the same extent as if each individual publication or patent application was specifically indicated and individually indicated by reference.

We claim:

1. A method of producing a clarified fermented beverage having a reduced or negligible level of organic acids, by neutralizing and removing organic acidic contaminants from a fermented beverage solution, comprising the steps of:
   a. providing a fermented beverage solution comprising at least one organic acidic contaminant;
   b. treating the fermented beverage solution by neutralizing the at least one organic acidic contaminant, by adding into the fermented beverage solution a sufficient amount of an alkaline treating agent to convert within the fermented beverage solution substantially all of the at least one organic acidic contaminant within the fermented beverage solution into a salt of the at least one organic acid contaminant, and forming a treated fermented beverage comprising the salt of the at least one organic acid contaminant; and
   c. separating the salt of the at least one organic acid contaminant formed in step (b) from the treated fermented beverage solution, thereby producing a clarified fermented beverage having a reduced or negligible level of organic acids.

2. The method according to claim 1 wherein the sufficient amount of alkaline treating agent neutralizes the fermented beverage solution to a pH of at least about 5.5, and up to about 8.5.

3. The method according to claim 2, wherein the alkaline treating agent comprises a Group I or Group II metal hydroxide.

4. The method according to claim 1, wherein the alkaline treating agent comprises up to about 50% by weight food grade sodium hydroxide.

5. The method according to claim 1, wherein the at least one organic acidic contaminant is lactic acid.

6. The method according to claim 1, wherein the fermented beverage solution is a bright beer.

7. The method according to claim 1, wherein the step of treating the fermented beverage solution comprises the steps of:
(i) providing a contained quantity of the fermented beverage solution comprising the at least one organic acidic contaminant;
(ii) titrating a sample of the contained quantity of fermented beverage solution with an alkaline treating agent sufficient to neutralize the at least one organic acidic contaminant in the sample to a salt form; and
(iii) adding a quantity of an alkaline treating agent to the contained quantity of fermented beverage solution to treat the fermented beverage solution by neutralizing the at least one organic acidic contaminant in the contained quantity to a salt form, wherein the quantity of the added alkaline treating agent is determined based on the titration of the sample.

8. The method according to claim 7, wherein the alkaline treating agent used to treat the contained quantity of fermented beverage solution is either the same alkaline treating agent used to titrate the sample, or is a different alkaline treating agent in a stoichiometric-equivalent quantity.

9. The method according to claim 1, wherein the step of neutralizing the at least one organic acidic contaminant is performed using an in-line, caustic dosing system, comprising:
a. a means for supplying the fermented beverage to the caustic dosing system;
b. at least one pH meter for detecting the pH of the fermented beverage;
c. a container for the alkaline treating agent;
d. a delivery means for providing liquid communication of the alkaline treating agent between the alkaline treating container and the supplied fermented beverage; and
e. a central programmable logic controller in communication with the at least one pH meter and the alkaline treating agent delivery means.

10. The method according to claim 9, wherein the at least one organic acidic contaminant in the fermented beverage solution is neutralized according to the following steps:
i) introducing a stream of the fermented beverage into the in-line caustic dosing system;
ii) detecting the pH of the fermented beverage stream using the at least one pH meter;
iii) determining a stoichiometric quantity of the alkaline treating agent necessary to neutralize the one or more organic acidic contaminants within the fermented beverage stream, using the central programmable logic controller; and
iv) dispensing the stoichiometric quantity of the alkaline treating agent from the alkaline treating agent container into the fermented beverage stream using the delivery means.

11. The method according to claim 10, wherein the in-line caustic dosing system comprises a pH meter upstream of the delivery of the alkaline treating agent and a pH meter downstream of the delivery of the alkaline treating agent into the fermented beverage stream.

12. A neutral malt base prepared from a bright beer, the neutral malt having a reduced or negligible level of organic acids relative to a level of the organic acids of the bright beer, the neutral malt base being colorless, odorless, flavorless and having a pH in the range of about 5.5 to about 6.5.

13. The neutral malt base according to claim 12, wherein the neutral malt base comprises at least about 10% and up to about 20%, by volume, ethyl alcohol.

14. The method according to claim 1, wherein the step of separating comprises filtering the salt of the organic acid contaminant from the treated fermented beverage.

15. The method according to claim 1, wherein the fermented beverage solution comprises at least about 10% and up to about 20%, by volume, ethyl alcohol.

16. A method of producing a clarified bright beer having a reduced or negligible level of an acidic contaminant, comprising the steps of:
a. providing a bright beer comprising an acidic contaminant;
b. adding an alkaline treating agent into the bright beer to neutralize within the bright beer the acidic contaminant, to form a neutralized bright beer containing a neutralized acidic contaminant; and
c. removing the neutralized acidic contaminant from the neutralized bright beer of step (b), thereby producing the clarified bright beer having a reduced or negligible level of the acidic contaminant.

17. The method according to claim 16, wherein the neutralized acidic contaminant is a salt.

18. The method according to claim 17, wherein the acidic contaminant comprises acetic acid and at least one organic acid selected from the group consisting of lactic acid, tartaric acid, propionic acid, and butyric acid.

19. The method according to claim 16, wherein the step of removing the neutralized acidic contaminant comprises filtering the neutralized acidic contaminant from the neutralized bright beer.

20. The method according to claim 16, wherein the addition of the alkaline treating agent raises the pH of the bright beer to at least about 5.5, and up to about 8.5.

21. The method according to claim 20, wherein the alkaline treating agent comprises a Group I or Group II metal hydroxide.

22. The method according to claim 16, wherein the clarified bright beer a pH in the range of about 5.5 to about 6.5.

23. The method according to claim 22, wherein the clarified bright beer comprises at least about 10% and up to about 20%, by volume, ethyl alcohol.

24. The method according to claim 16, further including a step of filtering, treating or decolorizing the clarified bright beer to produce a neutral malt base that is flavorless, odorless, and colorless, and has a reduced or negligible level of the acidic contaminant.

25. The method according to claim 16, wherein the step of removing the neutralized acidic contaminant further includes filtering, treating or decolorizing the neutralized bright beer to produce a neutral malt base that is flavorless, odorless, and colorless, and has a reduced or negligible level of the acidic contaminant.

26. The method according to claim 5, wherein the fermented beverage solution further comprises acetic acid.

27. The neutral malt base according to claim 13, wherein the one or more organic acids is selected from the group consisting of acetic acid, lactic acid, tartaric acid, propionic acid, butyric acid, and a mixture thereof.

* * * * *